(12) United States Patent
Beerling et al.

(10) Patent No.: US 9,696,246 B2
(45) Date of Patent: Jul. 4, 2017

(54) SENSOR SYSTEM WITH AN EXCHANGEABLE CARTRIDGE AND A READER

(75) Inventors: Bernardus Jozef Maria Beerling, Heeswijk-Dinther (NL); Jeroen Hans Nieuwenhuis, Waalre (NL); Petrus Johannes Wilhelmus Van Lankvelt, Boekel (NL); Wendela Meertens, Eindhoven (NL); Patrick Zuidema, Mierlo (NL)

(73) Assignee: KONINKLIJKE PHLIPS N.V., Eindhoven (NL)

( * ) Notice: Subject to any disclaimer, the term of this patent is extended or adjusted under 35 U.S.C. 154(b) by 436 days.

(21) Appl. No.: 14/113,832

(22) PCT Filed: Apr. 12, 2012

(86) PCT No.: PCT/IB2012/051801
§ 371 (c)(1),
(2), (4) Date: Oct. 25, 2013

(87) PCT Pub. No.: WO2012/147000
PCT Pub. Date: Nov. 1, 2012

(65) Prior Publication Data
US 2014/0041462 A1 Feb. 13, 2014

(30) Foreign Application Priority Data
Apr. 27, 2011 (EP) ..................................... 11163804

(51) Int. Cl.
*B01L 9/00* (2006.01)
*G01N 1/28* (2006.01)
(Continued)

(52) U.S. Cl.
CPC ........... *G01N 1/28* (2013.01); *G01N 21/0332* (2013.01); *G01N 21/552* (2013.01); *G01N 21/648* (2013.01); *G01N 2201/0221* (2013.01)

(58) Field of Classification Search
CPC ....... B01L 2300/0816; B01L 2200/027; B01L 9/527; B01L 2300/0636; C12Q 2565/629; G01N 27/3273
See application file for complete search history.

(56) References Cited

U.S. PATENT DOCUMENTS 6,930,292 B1 * 8/2005 Winther ............. B01L 3/50851
156/345.38
7,497,997 B2 * 3/2009 Glezer .................. B01L 3/5027
422/504

(Continued)

FOREIGN PATENT DOCUMENTS

| EP | 1115573 B1 | 7/2009 |
|----|------------|--------|
| EP | 2100667 A1 | 9/2009 |

(Continued)

*Primary Examiner* — David A Rogers

(57) ABSTRACT

A sensor system (100) includes a reader (150) with a sensor unit (155, 156) and an accommodation Space (151) for an exchangeable cartridge (110). The cartridge (110) is held in the accommodation space (151) by at least one contact element (111) which has an increased thermal resistance and/or a contact area of reduced size. Thus a more homogenous temperature distribution can be achieved within the cartridge (110), reducing distortions which might adversely affect optical measurements.

16 Claims, 3 Drawing Sheets

(51) Int. Cl.
  *G01N 21/03* (2006.01)
  *G01N 21/552* (2014.01)
  *G01N 21/64* (2006.01)

(56) References Cited

U.S. PATENT DOCUMENTS

| | | | |
|---|---|---|---|
| 7,776,583 B2 * | 8/2010 | Billadeau | G01N 33/523 422/68.1 |
| 8,005,280 B2 * | 8/2011 | Mott | G01N 21/75 382/128 |
| 8,537,237 B2 * | 9/2013 | Kahlman | G06T 5/002 348/222.1 |
| 8,841,076 B2 * | 9/2014 | Holmes | A61B 5/1411 356/39 |
| 9,040,288 B2 * | 5/2015 | Handique | B01L 3/5027 435/287.2 |
| 9,050,594 B2 * | 6/2015 | Williams | C12Q 1/68 |
| 9,081,001 B2 * | 7/2015 | Cook | G01N 21/66 |
| 2003/0064507 A1 | 4/2003 | Gallagher | |
| 2003/0180824 A1 * | 9/2003 | Mpock | C12Q 1/56 435/13 |
| 2007/0031283 A1 * | 2/2007 | Davis | A61B 5/14546 422/400 |
| 2007/0081163 A1 * | 4/2007 | Liang | G01N 21/253 356/445 |
| 2007/0224084 A1 * | 9/2007 | Holmes | A61B 5/1411 422/68.1 |
| 2007/0263207 A1 | 11/2007 | Mertz | |
| 2008/0124723 A1 * | 5/2008 | Dale | B01L 7/52 435/6.16 |
| 2008/0182301 A1 * | 7/2008 | Handique | B01L 3/502715 435/91.2 |
| 2009/0181228 A1 | 7/2009 | Gandhi | |
| 2010/0272608 A1 * | 10/2010 | Penterman | G01K 11/125 422/69 |
| 2010/0310423 A1 * | 12/2010 | Nieuwenhuis | B01L 3/5027 422/82.05 |
| 2010/0311183 A1 * | 12/2010 | Kahlman | G01N 27/745 436/166 |
| 2011/0093213 A1 * | 4/2011 | Van Lankvelt | G01N 1/02 702/23 |
| 2013/0109106 A1 * | 5/2013 | Klunder | B01L 3/0275 436/180 |
| 2013/0112018 A1 * | 5/2013 | Nieuwenhuis | G01N 35/00029 73/864.91 |
| 2013/0162981 A1 * | 6/2013 | Emeric | G01N 33/48 356/72 |
| 2013/0189794 A1 * | 7/2013 | Emeric | B01L 3/50273 436/501 |
| 2013/0203627 A1 * | 8/2013 | Moll | G01N 21/6486 506/9 |
| 2013/0309778 A1 * | 11/2013 | Lowe | B01L 3/502715 436/501 |
| 2014/0134602 A1 * | 5/2014 | Van Zon | G01N 21/552 435/5 |
| 2014/0263279 A1 * | 9/2014 | Vandersleen | B01L 7/00 219/477 |
| 2014/0286826 A1 * | 9/2014 | Neijzen | G01N 33/54373 422/82.05 |
| 2015/0187479 A1 * | 7/2015 | Van Lieshout | G01N 21/552 335/306 |

FOREIGN PATENT DOCUMENTS

| | | | | |
|---|---|---|---|---|
| NL | WO 2009066235 A1 * | 5/2009 | | G01N 21/552 |
| NL | WO 2009066236 A1 * | 5/2009 | | G01N 21/552 |
| NL | WO 2009087519 A2 * | 7/2009 | | G01J 5/02 |
| NL | WO 2010035204 A1 * | 4/2010 | | G01N 21/6428 |
| NL | EP 2230520 A1 * | 9/2010 | | B01L 3/502715 |
| WO | 9956954 A1 | 11/1999 | | |
| WO | 03099953 A1 | 12/2003 | | |
| WO | 2005010542 A2 | 2/2005 | | |
| WO | 2005010543 A1 | 2/2005 | | |
| WO | 2009016533 A2 | 2/2009 | | |
| WO | 2011036638 A1 | 3/2011 | | |

* cited by examiner

SENSOR SYSTEM WITH AN EXCHANGEABLE CARTRIDGE AND A READER

CROSS-REFERENCE TO PRIOR APPLICATIONS

This application is the U.S. National Phase application under 35 U.S.C. §371 of International Application No. PCT/IB2012/051801, filed on Apr. 12, 2012, which claims the benefit of European Application No. 11163804.5, filed on Apr. 27, 2011. These applications are hereby incorporated by reference herein.

FIELD

The invention relates to a sensor system comprising an exchangeable cartridge and a reader for making measurements in said cartridge. Moreover, it relates to a cartridge for such a sensor system.

BACKGROUND

U.S. Pat. No. 8,228,506 discloses a microelectronic sensor device for making optical examinations at a carrier, particularly for the detection of magnetic particles at a contact surface of the carrier by frustrated total internal reflection (FTIR). A particular laser modulation is used to minimize optical distortions arising from a thermal expansion of the carrier during measurements.

SUMMARY

It is an object to improve the accuracy and robustness of measurements made in an exchangeable cartridge, particularly if the temperature within the cartridge may be different from ambient temperature.

A first aspect relates to a sensor system for making examinations of a sample, particularly a sensor system for making measurements in a biological sample. The sensor system comprises two main components, namely:

An exchangeable cartridge with an "examination region" in which a sample can be provided and with (at least) a first and a second contact region where the cartridge can be contacted from outside. The cartridge is preferably a low-cost injection molded plastic part with microfluidic cavities in which a sample like blood or saliva can be accommodated. Due to its contamination with a sample, the cartridge is typically disposed after one use.

A reader with an accommodation space that can accommodate the aforementioned cartridge during an examination and with a sensor unit for making measurements in the examination region of the cartridge when it is in said accommodation space. With other words, the examination region by definition is or comprises that region of the cartridge in which measurements by the reader are (or can be) made when the cartridge is in the accommodation space. Furthermore, the first and second contact regions of the cartridge are those regions where the cartridge is contacted by the reader when being in the accommodation space.

The sensor system further comprises at least one contact element by which the cartridge is supported in the accommodation space (i.e. at least a part of the weight of the cartridge is carried by this element) and which comprises the first contact region or touches the first contact region (when the cartridge is in the accommodation space). The contact element may be a component of its own, but it is typically an integral part of the cartridge or of the reader. Moreover, it should be noted that the contact element is a subsidiary component in relation to the cartridge and the reader, i.e. its volume and/or weight is typically less than 50%, preferably less than 10% of the volume/weight of the cartridge.

Furthermore, the above components of the sensor system are designed such that there exists a first cross section through the contact element for which the thermal resistance is higher than the thermal resistance at any other (second) cross section which (i) cuts through the cartridge,
(ii) comprises the examination region, and
(iii) separates the first contact region from the second contact region.

Due to its higher thermal resistance, the first cross section will be called "high-resistance" cross section in the following. The second cross sections will accordingly be called "low-resistance" cross sections. Moreover, it should be noted that the thermal resistance of the low-resistance cross section refers to a state in which the cartridge is filled with a sample liquid, typically with a water based liquid. In particular, this liquid may be (pure) water. While the "low-resistance" cross sections shall include only those cross sections that comprise the examination region, the mentioned requirement for the contact element will preferably also hold with respect to the larger set of all cross sections that just fulfill conditions (i) and (iii).

The "thermal resistance" R of an area A (here the cartridge-area of a high-resistance or low—resistance cross section) is defined as the (inverse) proportionality constant in the following equation:

$$P = \text{grad } T/R \qquad (1)$$

The equation represents the heat flow P (unit: W) through the considered area A when a constant temperature gradient (grad T) is assumed across said area A. It should be noted that the value of the thermal resistance, R, is usually inversely proportional to the size of the considered area A.

A second aspect relates to a sensor system comprising:

An exchangeable cartridge with an examination region in which a sample can be provided and with a first contact region where it can be contacted.

A reader with an accommodation space for the cartridge and with a sensor unit for making measurements in the examination region of the cartridge.

At least one contact element by which the cartridge is supported in the accommodation space and which comprises or touches the first contact region, wherein the area of the first contact region is less than about 200 mm$^2$. Preferably, this area is smaller than about 100 mm$^2$, most preferably smaller than about 50 mm$^2$.

The sensor system according to the second aspect may preferably comprise the features of a sensor system according to the first aspect. The small contact area between cartridge and reader achieves an analogous effect as the design of the first sensor system, i.e. it yields a high thermal resistance in the contact element.

By the provision of a contact element bearing a cartridge within an accommodation space of a reader which has a high (relative) thermal resistance, the robustness and accuracy of measurements can be increased, particularly in assays that involve a temperature control within the cartridge. This is because whenever a quantity of heat flows through the cartridge such that it passes both the first and the second contact region (which are main areas through which the cartridge can exchange heat), the thermal resistance encountered in the high-resistance cross section of the contact element is larger than the thermal resistance encountered in any other low-resistance cross section. The contact element hence provides a bottleneck for the heat exchange due its high thermal resistance, which in turn causes a more homogeneous temperature distribution within the remainder of the cartridge. This allows particularly to keep thermal stress and distortions away from parts of the examination region of the cartridge that are critical for the measurements, for instance optical surfaces.

As the cartridge and the reader of the sensor system are physically and commercially independent items, the present concept can be applied to and realized in any of them. An exchangeable cartridge for a sensor system of the kind described above as a standalone element includes an examination region in which sample can be provided, a first and (optionally) a second contact region where it can be contacted, and at least one contact element by which the cartridge is supported and which comprises the first contact region. Furthermore, there exists a high-resistance cross section through the contact element for which the thermal resistance is higher than the thermal resistance at any other low-resistance cross section through the cartridge and the examination region that separates the contact regions. Alternatively or additionally, the area of the first contact region is less than about 200 $mm^2$.

Similarly, a reader for a sensor system of the kind described above comprises the following components:

An accommodation space for a cartridge.

A sensor unit for making measurements in the examination region of the cartridge.

At least one contact element for supporting the cartridge in the accommodation space, wherein said contact element (i) has a high-resistance cross section for which the thermal resistance is higher than the thermal resistance at any other low-resistance cross section through the examination region of the cartridge, and/or (ii) comprises a contact area between cartridge and reader of less than about 200 $mm^2$.

In the following, various preferred embodiments will be described that relate to the sensor system, the exchangeable cartridge, and/or the reader described above.

The first embodiment relates to preferred relative values for the thermal resistances. The thermal resistance of any low-resistance cross section through the cartridge shall optionally be less than 50%, preferably less than 10%, still more preferably less than 3%, and most preferably less than 1% of the thermal resistance of the high-resistance cross section in the contact element.

Preferably all regions of contact between the cartridge and the reader are designed as a "contact element" with high thermal resistance (at least all those regions that carry the weight of the cartridge and perhaps aside from regions where a controlled heat exchange is intended).

There are different ways how the thermal resistance of the contact element can be increased with respect to the remainder of the cartridge. For example, the contact element may be made of a material having a smaller thermal conductivity than the material of the residual cartridge. To allow for a cost-effective production of the cartridge from a single material, it is however preferred to achieve the increased thermal resistance of the contact element via its geometrical design. In a particular embodiment, the contact element therefore comprises a leg extending from the body of the cartridge or from the reader. The leg hence represents an element with a reduced cross section through which heat has to be transported, yielding an increased thermal resistance in a high-resistance cross section through the leg.

In a further development of the aforementioned embodiment, the leg may be provided with a tapered tip or a rounded tip at which contact between the cartridge and the reader is made. In case of a rounded tip, the radius of curvature is preferably between about 10 μm and 1000 μm. At a tapered or rounded tip, the cross section through which heat flow must take place is still further reduced (theoretically to a value of zero in a line or point contact), thus increasing the thermal resistance accordingly.

In another embodiment, the reader comprises a thermal control unit for exchanging heat with the cartridge when it is disposed in the accommodation space. The thermal control unit shall be able to generate heat (acting as a heater) and/or to absorb heat (acting as a cooler). With such a thermal control unit, the temperature within the cartridge can be controlled as desired, which is crucial for many biological assays. The thermal control unit is typically in thermal contact with the cartridge to allow for a precise and fast temperature regulation. In contrast to this, the residual contacts between the cartridge and the reader are preferably all made via contact elements with a high thermal resistance. The cartridge is hence thermally tightly coupled to the thermal control unit but only weakly coupled to the remainder of the reader.

The aforementioned thermal control unit is preferably disposed opposite to the at least one contact element. Hence heat is substantially transferred to (or taken from) the cartridge from one side, the cartridge being held in thermal isolation at the other side.

The sensor unit of the reader may be adapted to make measurements according to any measurement principle that is appropriate for a task at hand, and may for example be an optical, magnetic, mechanical, acoustic, thermal and/or electrical sensor unit. A magnetic sensor unit may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 (US 2008/0309329) or WO 2005/010542 A2 (US 2006/0194327), especially a GMR (Giant Magneto Resistance), a TMR (Tunnel Magneto Resistance), or an AMR (Anisotropic Magneto Resistance).

Most preferably, the sensor unit of the reader is adapted to make optical measurements. An optical sensor unit may for instance be adapted to detect variations in an output light beam that arise from a frustrated total internal reflection due to target particles at a sensing surface. Optical measurements are typically very sensitive to thermal influences, which affect for example the geometry of optical surfaces. Accordingly, these measurements will considerably profit from the advantages provided.

The application further relates to the use of the sensor system, the cartridge, or the reader described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects will be apparent from elucidated with reference to the embodiments described hereinafter.

In the drawings.

DETAILED DESCRIPTION OF EMBODIMENTS

Figure 1:
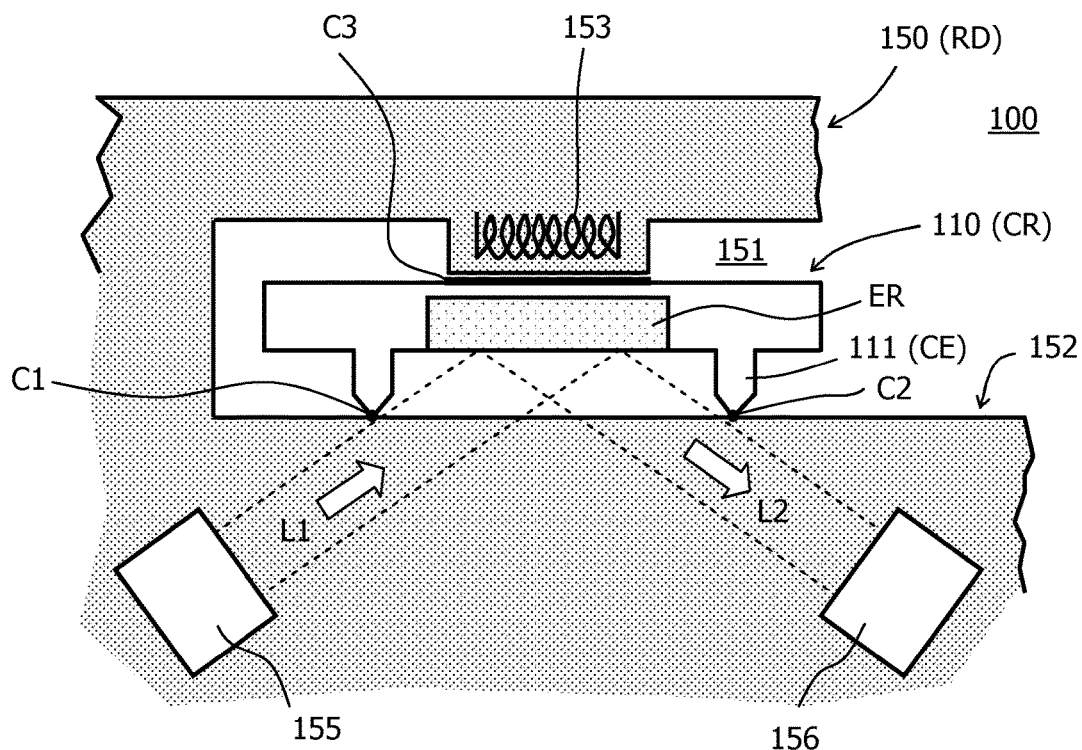
FIG. 1 schematically shows a side view of a sensor system.

FIG. 1 schematically shows a handheld sensor system 100. Similar to known sensor systems, this system 100 comprises two main components, namely:

An exchangeable (disposable) cartridge 110/CR with a examination region ER in which a sample can be provided. To this end, the examination region ER typically comprises microfluidic cavities that are not shown in detail in the Figure as they are irrelevant in the context of the present application. The cartridge has a top side and a bottom side, wherein two "contact elements" CE in the form of legs 111 extend downward from said bottom side.

A reader 150/RD providing an accommodation space 151 in which the cartridge 110 can be disposed during measurements. Furthermore, the reader 150 comprises a sensor unit, which consists in the illustrated example of a light generator 155 for directing an input light beam L1 towards the cartridge 110 and a light detector 156 for detecting an output light beam L2 returning from the cartridge. By definition, the "examination region" ER of the cartridge shall particularly comprise those zones of the cartridge that are reached by the input light beam L1 and/or the output light beam L2 (including by the evanescent waves generated therefrom). The optical measurements done by such a sensor unit may for example be based on frustrated total internal reflection (FUR) as it is described in more detail in the WO2009016533A2 (U.S. Pat. No. 8,228, 506).

The accommodation space 151 is constituted by some kind of cavity of the reader 150. The bottom of this cavity 151 provides a surface 152 on which the cartridge 110 can stand with its legs 111. The tips of the legs hence have (first) "contact regions" C1 and C2 at which the cartridge is contacted by the reader.

To get an accurate assay result with the sensor system 100, the temperature of the assay during a test is important, since assays are usually temperature dependent. Therefore the reader 150 is equipped with a heating unit 153 to control the temperature of the disposable cartridge 110. A heating plate of this heating unit 153 is pressed against the top of the cartridge 110 to transfer heat into the cartridge. The heating plate contacts the cartridge in a further ("second") contact region C3.

A side effect of the single sided heating is that the resulting temperature profile in the cartridge 110 may lead to a deformation of the cartridge, which adversely affects the optical read-out. The cartridge deformation is mainly a consequence of the uneven temperature profile in the cartridge. If one side of the cartridge is warmer than the other side of the cartridge, the warmer side of the cartridge will expand more, leading to mechanical deformation.

It is therefore an object of the invention to improve the robustness of measurements with a sensor system of the kind described above. According to the invention, this is achieved by an improved temperature profile in the cartridge, such that the critical elements of the cartridge show minimal deformation as a consequence of local variations in temperature.

A significant reduction in undesired mechanical deformation of the cartridge may be achieved by locally increasing the thermal resistance in a specific part of the cartridge that has no direct optical function, such that the majority of the temperature variation is located in this specific part of cartridge, leading to a reduced deformation in the optically active parts of the cartridge.

In the embodiment shown in FIG. 1 this is achieved by defining the V-shaped contact element 111 of the cartridge at the interface to the read-out instrument 150. This results in less thermo-mechanical deformation of the cartridge which results in more stable optical behavior in the analytical optical instrument. It should be noted that V-shaped tapered tips could similarly be formed on the reader 150.

Due to the V-shaped tips of the legs 111, the contact area between cartridge 110 and reader 150 can considerably be reduced for each contact region C1, C2 at which weight of the cartridge is supported. For example, a typical feature size would be two tips being 100 μm wide and 4 cm long, resulting in a contact area of about 8 mm². The contact area for a cartridge without extra tips (or ridges, cf. FIG. 7) on the ribs would be about 80 mm² (two times 1 mm wide and 40 mm long). In contrast to this, a typical cartridge (10 mm wide and 40 mm long) completely without ribs would have a contact area of about 400 mm².

Figure 2:
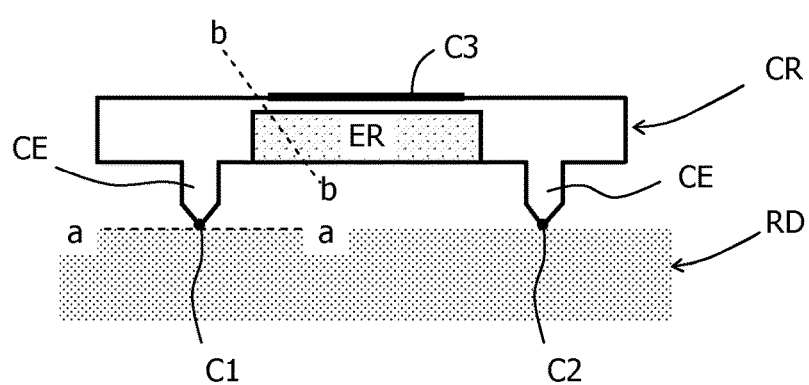
FIG. 2 schematically shows a cartridge with tapered legs on a reader.

FIG. 2 is a separate illustration of the components that are essential for the effects achieved by the present invention. These are:

The cartridge CR with its examination region ER and (three) contact regions C1, C2, C3 at which it can be contacted by the reader RD.

The reader RD with the surface by which the cartridge is supported.

The cartridge CR comprises two "contact elements" CE, i.e. legs with tips, via which it is supported on/in the reader RD and which comprise the contact regions C1 and C2, respectively. For each contact element CE, the following requirements are fulfilled (here expressed for the contact element with contact region C1): There exists a "high-resistance" cross section a-a through the contact element CE for which the thermal resistance is higher than the thermal resistance at any other "low-resistance" cross section b-b that (i) cuts through the complete cartridge CR, (ii) comprises the examination region ER, and (iii) separates the contact region C1 of the considered contact element CE from any one of the other contact regions (i.e. C2, C3).

Figure 3:
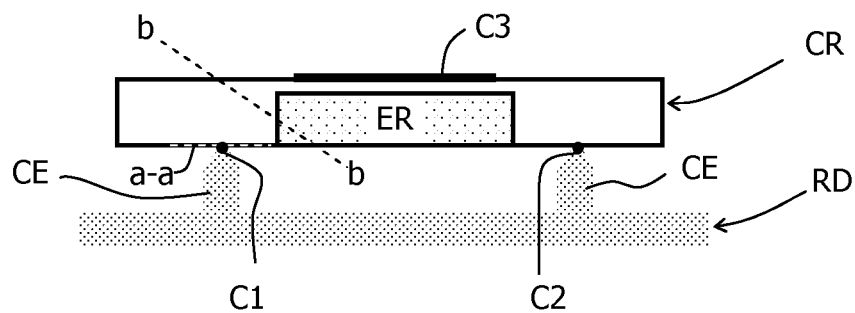
FIG. 3 schematically shows a cartridge on a reader with tapered posts.
Figure 4:
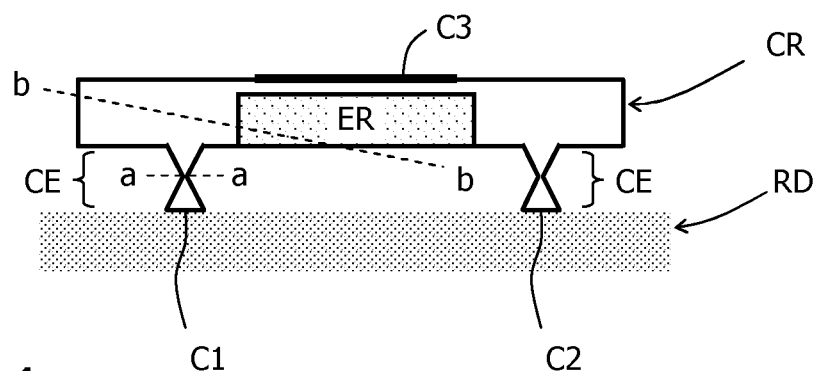
FIG. 4 schematically shows a cartridge with constricted legs on a reader.
Figure 5:
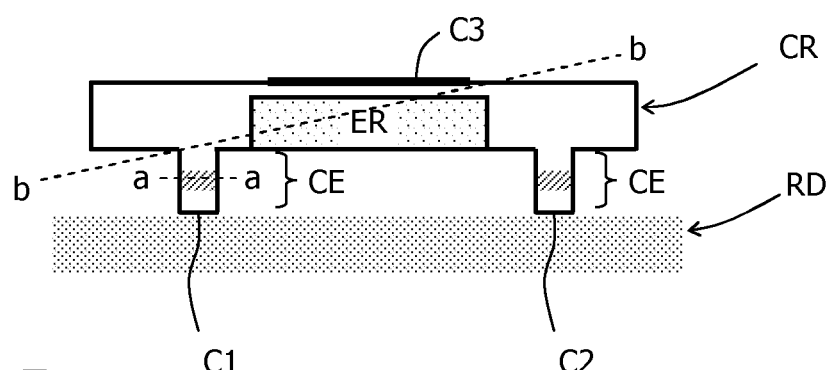
FIG. 5 schematically shows a cartridge with legs comprising in insulating zone on a reader.

In the shown example, the high-resistance cross section a-a lies such that it comprises the respective contact region C1 of the contact element CE. For the low-resistance cross section b-b, one example is shown in FIG. 2. Other examples are shown in FIGS. 3-5. The cross sections are typically planar. Moreover, they usually cut connected areas out of the cartridge.

Whenever heat is exchanged between the reader RD and the cartridge CR, this will take place by heat flow via one of the contact regions C1, C2, or C3 (neglecting heat flow across the surface of the cartridge into ambient air). The above requirements hence mean that any heat flowing via contact region C1 to any other contact region (i.e. C2 and/or C3) encounters the largest thermal resistance in the contact element CE, namely in the high-resistance cross section a-a. Hence the largest temperature gradient will occur here, while temperature in the examination region ER will be more homogenous.

It should be noted that the "thermal resistance" R of a cross section (a-a or b-b) is defined via equation (1), P=grad T/R, assuming a constant temperature gradient grad_T across the area of the cross section. The thermal resistance R is measured in K·m/W. In a homogenous material (or, more generally, in a body with constant thermal conductivity λ), the thermal resistance R of any cross section through the body is just R=c/A with c being a constant and A being the area of the considered cross section. Comparison of thermal resistances of different cross sections is hence tantamount to a comparison of the corresponding cross sectional areas.

FIG. 3 illustrates a modification of the sensor system of FIG. 2. The contact elements CE are now posts with tapered tips that are integral to the reader RD. The thermal effects are of course similar to those of FIG. 2.

FIG. 4 illustrates another modification of the sensor system of FIG. 2. Here the contact elements CE comprise constrictions of their diameter. Now the high-resistance cross section a-a passes through said constrictions, not through the contact regions C1, C2.

FIG. 5 illustrates a modification of the sensor system of FIG. 4. Instead of constrictions, the contact elements CE here comprise zones with a lower thermal conductivity. These zones may for example be achieved by the inclusion of a thermally insulating material.

Figure 6:
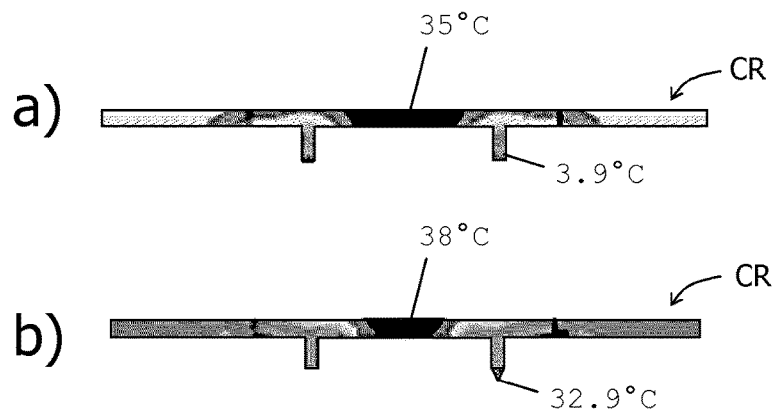
FIG. 6 shows simulated temperature profiles for a) a cartridge with blunt legs and b) a cartridge with tapered legs.

FIG. 6 illustrates the advantages that may be achieved by temperature profiles obtained at 2° C. ambient temperature within a cartridge CR having legs with blunt ends (FIG. 6a) and a cartridge CR having tapered legs according to the above description (FIG. 6b).

Furthermore, the temperatures at the center of the cartridge and at its legs are indicated in FIG. 6. These temperatures and the temperature profiles show that the temperature is less dependent on ambient temperature for the cartridge with V-shaped tips and that a more homogenous temperature distribution is achieved for this cartridge. This results in much less thermo-mechanical deformation due to thermal gradients in case of the V-shaped skis.

Figure 7:
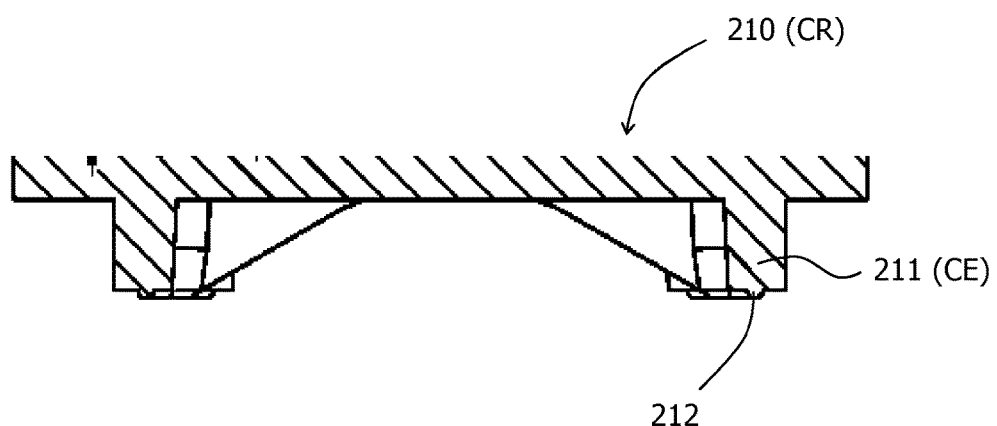
FIG. 7 shows an alternative embodiment of the cartridge comprising legs with a ridge.

FIG. 7 shows the bottom side of another embodiment of a cartridge 210. In this embodiment, the resistance is locally increased by defining a small, rounded ridge 212 on the bottom of the legs 211 of the cartridge. The radius of curvature of the ridge 212 may typically be about 100 μm. The main advantage of this embodiment is that it is very easy to manufacture at low cost.

In summary, the undesired deformation of a disposable cartridge as a consequence of a temperature profile inside the cartridge is significantly improved by locally increasing the thermal resistance of a non-critical part of the cartridge, such that this non-critical part absorbs the majority of the temperature drop. As a consequence the optical performance of the critical parts of the cartridge is no longer compromised due to mechanical deformation.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor system comprising:
an exchangeable cartridge with an examination region in which a sample can be provided and with a first and a second contact region where it can be contacted;
a reader with an accommodation space for the cartridge and with a sensor unit for making measurements in the examination region of the cartridge;
at least one contact element by which the cartridge is supported in the accommodation space and which comprises or touches the first contact region,
wherein there exists a "high-resistance" cross section (a-a) through the contact element for which the thermal resistance is higher than the thermal resistance at any other "low-resistance" cross section (b-b) that
(i) cuts through the cartridge,
(ii) comprises the examination region, and
(iii) separates the first contact region from the second contact region,
wherein the thermal resistance at any low-resistance cross section (b-b) is less than 10%, preferably less than 3% of the thermal resistance at the high-resistance cross section (a-a); and
wherein the at least one contact element comprises a leg extending between the cartridge and the reader, and wherein the leg includes a zone of insulating material configured to increase a resistance to heat flow through the leg.

2. The sensor system according to claim 1, wherein the area of the first contact region is less than about 200 mm$^2$.

3. The sensor system according to claim 1, wherein leg has a tapered tip.

4. The sensor system according to claim 1, wherein the leg has a rounded tip with a radius between 10 μm and 1000 μm.

5. The sensor system according to claim 1, wherein the reader includes a thermal control unit for exchanging heat with the cartridge.

6. The sensor system according to claim 5, wherein the thermal control unit is disposed on a side of the cartridge opposite to the at least one contact element.

7. The sensor system according to claim 1, wherein the sensor unit of the reader makes optical measurements.

8. The sensor system according to claim 1, wherein the cartridge and the sensor unit are used for molecular diagnostics, biological sample analysis, chemical sample analysis, food analysis, and/or forensic analysis.

9. An exchangeable cartridge comprising:
an examination region in which a sample can be received;
contact regions ($C_1$, $C_2$, $C_3$) which can be contacted by a reader;
at least one contact element extending from a first side of the cartridge and supporting the cartridge on a surface of the reader, wherein the at least one contact element comprises a first of the contact regions;
wherein the at least one contact element includes a zone of thermally resistive material such that thermal resistance through the at least one contact element between the first side of the cartridge and the surface of the reader is higher than the thermal resistance of other portions of the cartridge,
wherein the at least one contact element includes legs extending from a first side of the cartridge, the zone of thermally resistive material being disposed in the legs.

10. A sensor system comprising:
a reader including a heater element and a sensor surface and configured to define a cartridge accommodation space between the heater element and the sensor surface;
an exchangeable cartridge configured to be received in the cartridge accommodation space, the cartridge including:
  an examination region configured to receive a sample,
  a first contact element disposed adjacent the examination region and configured to conduct heat into the cartridge from a first side to heat the sample in the examination region,
  at least two legs disposed at a second side of the cartridge opposite to the first side of the cartridge, the legs being configured to support the cartridge on the sensor surface,
  a thermal inhibiting structure associated with the legs and configured to inhibit heat flow from the cartridge to the sensor surface such that thermal gradients across the cartridge are inhibited.

11. The sensor system according to claim 10, wherein the thermal inhibiting structure includes thermally resistive material disposed in the legs.

12. The sensor system according to claim 11, wherein the thermal resistive material inhibits heat flow more than the cartridge inhibits heat flow.

13. The sensor system according to claim 10, wherein the thermal inhibiting structure includes an element extending from the sensor surface with a tapered tip.

14. The sensor system according to claim 10, wherein the thermal inhibiting structure includes a region centrally along the legs with a constricted diameter.

15. The sensor system according to claim 10, wherein the thermal inhibiting structure includes tapered tips defined at ends of the legs.

16. The sensor system according to claim 10, wherein the thermal inhibiting structure includes rounded ridges extending from ends of the legs.

* * * * *